United States Patent [19]

Fiocco

[11] Patent Number: 4,519,901

[45] Date of Patent: May 28, 1985

[54] EXTRACTIVE SEPARATION PROCESS

[75] Inventor: Robert J. Fiocco, Summit, N.J.

[73] Assignee: Exxon Research & Engineering Co., Florham Park, N.J.

[21] Appl. No.: 539,122

[22] Filed: Oct. 5, 1983

Related U.S. Application Data

[63] Continuation-in-part of Ser. No. 332,194, Dec. 18, 1981, abandoned.

[51] Int. Cl.³ ............................................. C10G 21/00
[52] U.S. Cl. ................................... 208/321; 208/322; 585/804
[58] Field of Search ................. 208/321, 322, 327; 585/804, 807, 833

[56] References Cited

U.S. PATENT DOCUMENTS

| | | | |
|---|---|---|---|
| 2,261,799 | 11/1941 | Franklin, Jr. | 208/321 |
| 2,305,038 | 12/1942 | Schumacher | 208/321 |
| 2,727,848 | 12/1955 | Georgian | 208/321 |
| 3,422,163 | 1/1969 | Asselin | 585/807 |
| 3,428,553 | 2/1969 | Shiah | 208/321 |
| 3,436,435 | 4/1969 | Van Tassell | 208/321 |
| 3,520,946 | 7/1970 | Broughton | 585/804 |
| 3,560,374 | 2/1971 | Gruia | 208/321 X |
| 4,081,355 | 3/1978 | Preusser et al. | 208/322 |

Primary Examiner—Delbert E. Gantz
Assistant Examiner—Glenn A. Caldarola
Attorney, Agent, or Firm—Edward H. Mazer; Robert J. North

[57] ABSTRACT

An improved extractive separation process is described. This process is directed at splitting the feed and/or recycle stream to the extraction zone, to improve extraction zone performance. A further improvement may be achieved if at least a portion of the recycle stream is added to the extraction zone above the point where all the feed stream is added to the extraction zone.

12 Claims, 1 Drawing Figure

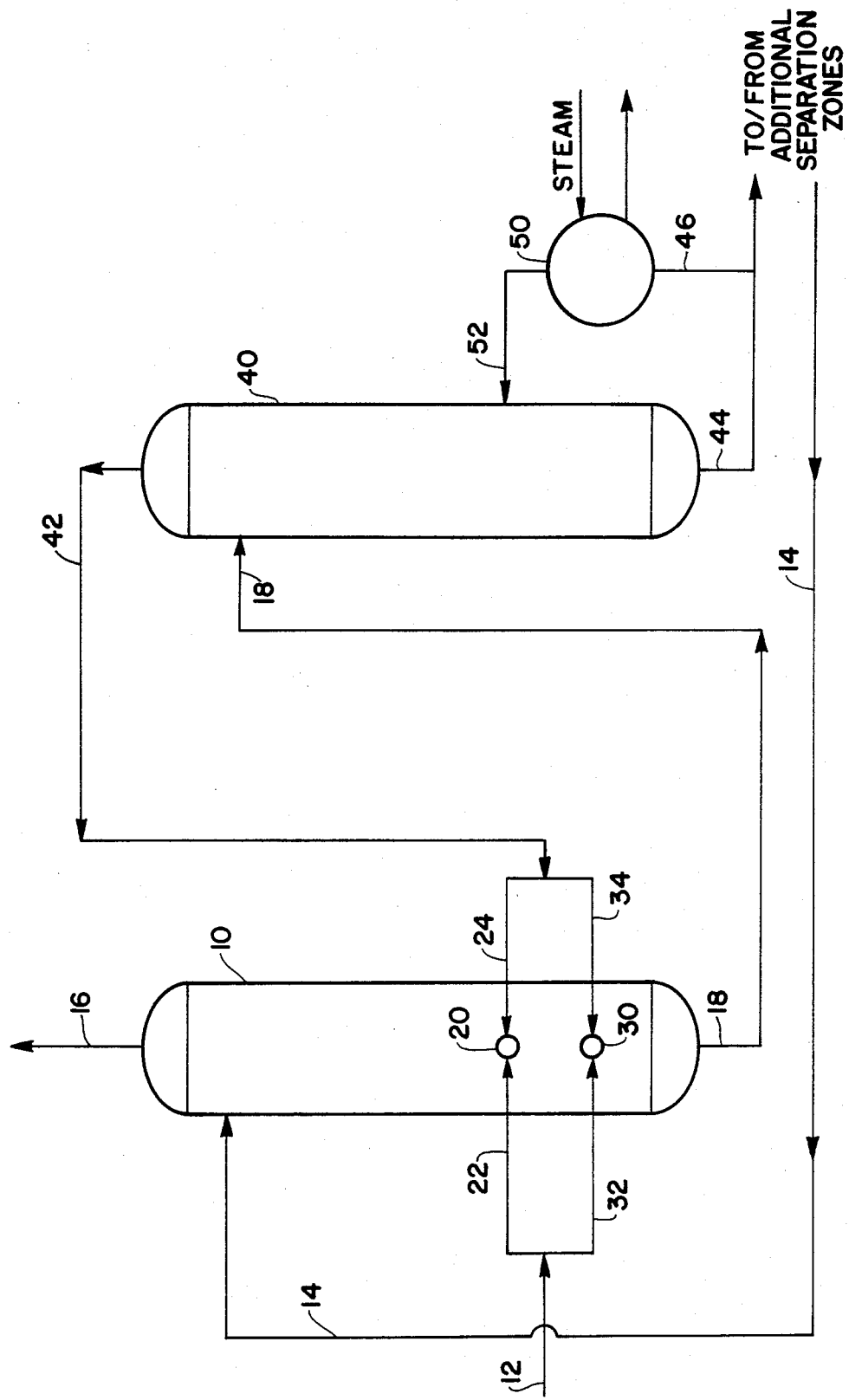

EXTRACTIVE SEPARATION PROCESS

CROSS-REFERENCE TO RELATED APPLICATIONS

This application is a continuation-in-part of Ser. No. 332,194, filed Dec. 18, 1981, now abandoned.

BACKGROUND OF THE INVENTION

This invention is directed at an improved extractive separation process. More specifically, the present invention is directed at an improved method for directing feed and/or recycle streams into an extraction zone to improve the extraction zone performance.

In the separation of a mixture of components, one or more unit operations may be utilized. The particular unit operation normally is selected after a consideration of several variables, including the desired purity of the separated fractions, capital equipment cost, equipment reliability and operating costs. In many separation operations, extractive separation may be the preferred method of separation. Typically, a solvent having the desired affinity for one or more of the feed and/or recycle stream components is passed through the extraction zone countercurrently to the feed and/or recycle streams to effect the separation. For example, in the separation of aromatics, such as benzene, toluene, and xylene (BTX) from non-aromatics, such as hexane, heptane, and isoheptane, the feed and/or recycle stream may be contacted with a solvent such as sulfolane (tetrahydrothiophene-1,1-dioxide), tetraethylene glycol, phenol, dimethysulfoxide, furfural, or N-methyl pyrrolidone. In the preparation of a lube oil basestock from a hydrocarbon feedstock the hydrocarbon feedstock may be extracted with a solvent such as phenol, N-methyl pyrrolidone and furfural.

In the conventional process, the solvent typically is introduced substantially at the top of the extraction zone, flows downwardly, and exits at the bottom enriched with the extracted component. The hydrocarbon inlet feedstream typically is introduced at a single location at or near the bottom of the extraction zone, flows upwardly, and exits near the top of the extraction zone with a reduced concentration of the extracted component. The inlet recycle stream, if present, typically is introduced at a single location below the hydrocarbon feed location to achieve a backwashing effect for displacing certain components from the solvent before the solvent exits from the base of the extractor. In the extractive separation of aromatics from non-aromatics, recycle stream components may displace from the aromatic-rich solvent into the raffinate certain non-aromatic components which would be more difficult to remove from the BTX product in downstream purification steps. This recycle stream typically may be a product stream from a downstream purification stage which removes non-aromatics from the aromatic products.

In many extractive operations, it may be desired to improve the capacity and/or separation achieved in the extraction zone of new or existing extractive separation zones without the need for additional processing equipment and without increasing the size and/or operating costs. In other operations, upstream modifications or changes in feeds may have altered the composition or flow rates to the extraction zone from those utilized in the original design of the extraction zone.

Accordingly, it is desirable to provide a reliable, flexible process which may even be retrofitted to existing extraction zones to permit increased throughput rates without adversely affecting product quality and without causing a significant increase in operating costs.

It also is desirable to provide a process which may improve the feed separation in an extraction zone.

The subject invention is directed at the discovery that the efficiency of an extractive separation process may be improved by passing the feedstream and/or recycle stream into the extraction zone simultaneously through a plurality of spaced-apart nozzles rather than through a single nozzle. It also has been discovered that the capacity and/or separation efficiency of an extractive separation in which a recycle stream from a downstream product purification step is recycled to the extraction zone may be improved if at least a portion of the recycle is added to the extraction zone at a location above the location at which all the feed is added to the extraction zone. This improvement in extraction zone efficiency permits an increase in product quality or through-put.

SUMMARY OF THE INVENTION

The present invention is directed at an extraction separation of the type wherein:
  A. an inlet feed stream having a first component and a second component is directed into an extraction zone;
  B. a solvent selectively miscible with one of the components is directed into the extraction zone at a spaced apart location from the point of addition of the feed stream;
  C. the feed stream and solvent stream pass substantially countercurrently through the extraction zone to produce an extract product stream relatively rich in the first component and a raffinate product stream relatively rich in the second component; and
  D. a separate recycle stream produced by subsequent processing of at least one of the extraction zone product streams is returned to the extraction zone, the improvement comprising the addition of at least a fraction of the recycle stream to the extraction zone at a location above the location at which all the feed is added to the extraction zone.

In a preferred embodiment the first component comprises an aromatic selected from the group consisting of benzene, toluene and xylene and mixtures thereof. The second component preferably comprises a non-aromatic. The solvent preferably is selectively miscible with the aromatic component and is selected from the group consisting of sulfolane, tetraethylene glycol, phenol, dimethylsulfoxide, furfural, N-methyl pyrrolidone and mixtures thereof. Preferably at least 5 wt. % of the recycle stream and more preferably at least 25 wt.% of the recycle stream is added to the extraction zone at a location above the location at which all the feed is added to the extraction zone.

BRIEF DESCRIPTION OF THE DRAWING

The FIGURE is a simplified schematic flow drawing of one method for practicing the subject invention.

DETAILED DESCRIPTION OF THE INVENTION

The subject invention may be of utility in applications where extraction zone efficiency is hampered by extraction zone hydraulics, particularly in those applications where feed and/or recycle inlets are overloaded due to high hydrocarbon or solvent flow rates and/or deficiencies in the design of the extraction zone internals. This invention may be of particular utility for feeds having a relatively high non-aromatics content which are at least partially soluble in the solvent and which are difficult to remove in subsequent purification operations.

Referring to the FIGURE, an extractive separation process is shown. In the FIGURE all equipment, valves, piping and controls not necessary for an understanding of the present invention have been omitted for clarity. The internal construction of extractive separation zone 10 may be of conventional design, having trayed, packed, baffled or mechanically agitated internals. A feedstream such as a hydrocarbon feedstock is shown passing through line 12 and thence through line 22 and nozzle 20, and/or through line 32 and nozzle 30 into extraction zone 10. Solvent is shown entering zone 10 through line 14. Raffinate comprising substantially no aromatics exits zone 10 through line 16 for further processing (not shown) while aromatics-rich extract containing some non-aromatic impurities exits through line 18. The extract passes into separation zone 40 having reboiler 50. The extract is separated into an overhead fraction and a bottoms fraction. The overhead fraction, comprising most of the non-aromatics, is condensed and recycled through line 42. The recycle then passes through line 24 and nozzle 20 and/or line 34 and nozzle 30 into extraction zone 10. Bottoms from separation zone 40 exit the base of zone 40 through line 44 for further separation of the solvent from the feed component in additional separation zones (not shown) before the solvent is returned to zone 10 through line 14. Part of the bottoms from line 44 are recycled through line 46 into reboiler 50 and thence through line 52 back to zone 40 to provide heat for the separation.

The subject invention has been used to improve the operation of an extraction zone used for the separation of benzene, toluene and xylene from non-aromatics using sulfolane as the solvent. In the application of this invention described hereinafter, zone 10 comprised a commercial extraction zone having perforated trays. Inlet lines 22 and 32 for feed, and 24 and 34 for recycle, permitted both the feed and/or recycle streams to be split before entering the extraction zone, rather than entering zone 10 through only one location. Nozzles 20 and 30 preferably are disposed a minimum of one tray apart. Preferably, at least 5 wt.% of the split stream is passed through each nozzle location. One measure of the efficiency of the extractive aromatics-non-aromatics separation process is the percent non-aromatics in a downstream BTX product line. Table I shows the net increase in the non-aromatics content of the downstream BTX product line over a base amount as a function of net increase in feed rate at constant recycle, where all the feed was added through line 32 and all the recycle was added through line 34 into nozzle 30. Table II illustrates that the net increase inn the non-aromatics content of the downstream BTX product line is much lower than the values reported in Table I when the feed rate is increased over a base amount and the feed is split, with a fraction of the feed being added through line 22 and a fraction through line 32, while all the recycle enters through line 34. From a comparison of Tables I and II, it can be seen that splitting the feed permits a greater increase in feed rate for substantially the same increase in the concentration of non-aromatics in the downstream BTX product line. In Table I, an increase in the feed rate of about 8.2% from the base rate resulted in an increase of 0.10 wt.% in the non-aromatics concentration in the downstream BTX product line. By comparison, when the feed was split, the data of Table II illustrate that an increase of about 16.4% from the base rate resulted in only a 0.11 wt.% non-aromatics content in the downstream BTX product line.

TABLE I

INCREMENTAL CHANGE IN NON-AROMATICS CONTENT OF BTX PRODUCT WHEN ALL FEED ADDED THROUGH ONE FEED LOCATION

| Feed Rate Increase to Extraction Zone Through Line 32 (wt. %) | Increase in Wt. % Non-Aromatics in Downstream BTX Product Line As Compared to Base Value |
|---|---|
| 2.7 | 0 |
| 8.2 | 0.10 |

TABLE II

INCREMENTAL CHANGE IN NON-AROMATICS CONTENT OF BTX PRODUCT WHERE FEED ADDED THROUGH TWO INLET LOCATIONS

| Wt. % Increase in Feed Rate Through Line 22 Over Base Rate in which All Feed Added Through Line 32 | Increase in Wt. % Non-Aromatics in Downstream BTX Product Line as Compared to Base Value |
|---|---|
| 0 | 0 |
| 2.7 | 0 |
| 3.7 | 0.03 |
| 6.4 | 0.04 |
| 9.1 | 0.04 |
| 12.8 | 0.05 |
| 15.5 | 0.08 |
| 16.4 | 0.11 |

As shown by the data in Table III, from another set of runs a much more dramatic increase in extraction zone performance could be realized by directing at least a fraction of the recycle through line 24 into zone 10. The data indicate that where all the feed was added through line 32 and all the recycle through line 34, increasing the feed rate above the base rate resulted in a significant increase in the downstream non-aromatics content in the BTX product line. Increasing the feed rate to extraction zone 10 through line 32 by 12.3 and 21.5 wt.% resulted in increases of 0.04 and 0.14 wt.%, respectively, in the downstream non-aromatics content in the BTX product line. However, other data in this table demonstrated that splitting the recycle stream permitted a significant increase in the feed rate to zone 10 without causing a significantly adverse effect on BTX product line quality. Where recycle stream 42 was split such that approximately 25 wt.% passed through line 24 and nozzle 20, and approximately 75 wt.% passed through line 34 and nozzle 30 while the feed rate was held constant through line 32, the non-aromatics content of the BTX product line declined by 0.05 wt.%. With this same split of the recycle stream through lines 24 and 34 and with all the feed added through line 32, it was possible to increase the feed rate by more than 26 wt.% over the base rate while increasing the non-aromatics content of the BTX product line by only 0.02 wt.% over the base rate. Thus, it may be seen that splitting the recycle stream and adding at least a fraction of the recycle stream above the location at which all the feedstream is added permitted a very significant increase in product quality and/or in through-put.

In the extractive separation of benzene, toluene and xylene, the component most sensitive to the effectiveness of the extractive separation is xylene. Utilization of the above-noted process, in which a fraction of the recycle stream was split, produced about a 6% increase in xylene recovery as compared to a conventional process at comparable feed rates in which the recycle stream was not split. Thus, the addition of a fraction of the recycle above the location at which all the feed is added produced a downstream BTX product line having a reduced non-aromatics content while simultaneously increasing the xylene recovery as compared to a conventional process in which the recycle was not split.

While the examples have described a specific extraction system, it is clear that this invention is applicable to other extraction operations.

Although the invention has been described with respect to specific compounds and a specific embodiment, it will be understood that this disclosure is intended to cover any variations, uses or adaptations of the invention including such departures from the present disclosure as come within known or customary practice in the art to which this invention pertains and which fall within the scope of the invention.

TABLE III

INCREMENTAL CHANGE NON-AROMATICS CONTENT OF BTX PRODUCT WHEN RECYCLE ADDED THROUGH TWO INLET LOCATIONS

| Wt. % Increase in Feed Rate to Extraction Zone Over Base Rate; All Feed Added Through Line 32 | Split of Recycle Stream to Extraction Zone (wt. %) | | Change in Wt. % Non-Aromatic in Downstream BTX Product Line |
|---|---|---|---|
| | Through Line 34 | Through Line 24 | |
| 0 | 100 | 0 | 0 |
| 12.3 | 100 | 0 | +0.04 |
| 21.5 | 100 | 0 | +0.14 |
| 0 | 75 | 25 | −0.05 |
| 1.5 | 75 | 25 | −0.06 |
| 26.2 | 75 | 25 | +0.02 |

What is claimed is:

1. In an extractive separation of the type wherein:
   A. an inlet feed stream having an aromatic component selected from the group consisting of benzene, toluene, xylene, or mixtures thereof, component and a non-aromatic component is directed into an extraction zone;
   B. a solvent selectively miscible with one of said aromatic components is directed into the extraction zone at a spaced apart location from the point of addition of the feed stream;
   C. the feed stream and solvent stream pass substantially countercurrently through the extraction zone to produce an extract product stream relatively rich in the aromatic component and a raffinate product stream relatively rich in the non-aromatic component; and
   D. a separate recycle stream produced by subsequent processing of at least one of the extraction zone product streams is returned to the extraction zone, the improvement comprising the addition of at least a fraction of the recycle stream containing substantially all of the non-aromatic component of the extract product stream to the extraction zone at a location above the location at which all the feed is added to the extraction zone.

2. The method of claim 1 wherein the solvent is added to the extraction zone at a location above the location at which the feed is added to the extraction zone.

3. The method of claim 2 wherein the feed stream is added to the extraction zone through a plurality of locations and wherein the recycle stream is added to the extraction zone at a location above all of the locations at which the feed is added.

4. The method of claim 2 wherein at least 5 wt.% of the recycle stream is added to the extraction zone at a location above the location at which all the feed is added to the extraction zone.

5. The method of claim 4 wherein approximately 25 wt.% of the recycle stream is added to the extraction zone.

6. The method of claim 4 wherein the solvent is selectively miscible with the aromatic component.

7. The method of claim 6 wherein the solvent is selected from the group consisting of sulfolane, tetraethylene glycol, phenol, dimethyl-sulfuoxide, furfural, N-methyl pyrrolidone and mixtures thereof.

8. The method of claim 7 wherein the extraction zone comprises a trayed extraction zone, and wherein at least a fraction of the recycle stream is added a minimum of one tray above the location where all the feed stream is added to the extraction zone.

9. The method of claim 7 wherein the extraction zone comprises a baffled extraction zone.

10. The method of claim 7 wherein the extraction zone comprises a packed extraction zone.

11. The method of claim 7 wherein the extraction zone has mechanically agitated internals.

12. In an extractive separation of an aromatic component selected from the group consisting of benzene, toluene, xylene and mixtures thereof, from a non-aromatic component of the type wherein:
   A. an inlet feed stream having said aromatic component and a non-aromatic component is directed into a trayed extraction zone;
   B. a solvent selectively miscible with the aromatic component is directed into the extraction zone at a spaced apart location above the point of addition of the feed stream;
   C. the feed stream and solvent stream pass substantially countercurrently through the extraction zone to produce an extract product stream relatively rich in the aromatic component and a raffinate product stream relatively rich in the non-aromatic component; and
   D. a separate recycle stream produced by subsequent processing of at least one of the extraction zone product streams is returned to the extraction zone, the improvement comprising the addition of at least 5 wt.% of the separate recycle stream to the extraction zone at a location a minimum of one tray above the location at which all the feed is added to the extraction zone.

* * * * *